United States Patent [19]
du Plessis et al.

[11] Patent Number: 5,962,363
[45] Date of Patent: Oct. 5, 1999

[54] CATALYST SYSTEM SUITABLE FOR USE IN THE METATHESIS OF UNSATURATED HYDROCARBONS

[75] Inventors: Jan Adriaan Kruger du Plessis; Hermanus Cornelius Moolman Vosloo; Alta Jansen van Rensburg, all of Potchefstroom, South Africa

[73] Assignee: Sasol Technology (Proprietary) Limited

[21] Appl. No.: 08/979,289

[22] Filed: Nov. 26, 1997

Related U.S. Application Data

[62] Division of application No. 08/708,173, Sep. 6, 1996
[60] Provisional application No. 60/003,481, Sep. 8, 1995.

[51] Int. Cl.$^6$ ...................................................... B01J 31/02
[52] U.S. Cl. ........................... 502/154; 502/150; 502/152; 502/171; 502/349; 502/352
[58] Field of Search ..................................... 502/150, 152, 502/154, 171, 349, 352

[56] References Cited

U.S. PATENT DOCUMENTS

| | | |
|---|---|---|
| 3,974,233 | 8/1976 | Lawrenson ............................... 585/647 |
| 4,399,057 | 8/1983 | Hensley, Jr. et al. .................... 252/435 |
| 4,504,593 | 3/1985 | Trinh Dinh et al. ..................... 502/154 |
| 5,026,936 | 6/1991 | Leyshon et al. ......................... 585/643 |

OTHER PUBLICATIONS

K.J. Ivin et al. "Mechanism for the Stereospecific Polymerization of Olefins by Zeigler–Natta Catalysts" J.C.S. Chem. Comm. 1978, pp. 604–606. No month available.

Ahn, et al "A Novel Metathesis Catalyst Consisting of Non–Transition Elements" Chemistry Letters. pp. 503–506. 1992 no month available.

Ivin, K.J. "Olefin Metathesis" Ch. 2; pp. 13–14; Academic Press (London), 1983 no month available.

*Primary Examiner*—Elizabeth D. Wood
*Attorney, Agent, or Firm*—Ladas & Parry

[57] ABSTRACT

A catalyst system, which is suitable for use in the metathesis of unsaturated hydrocarbons, comprises silica, alumina and an alkyl tin compound in intimate contact with one another. The catalyst system is characterized thereby that it contains no transition metal such as tungsten, molybdenum or rhenium.

10 Claims, 1 Drawing Sheet

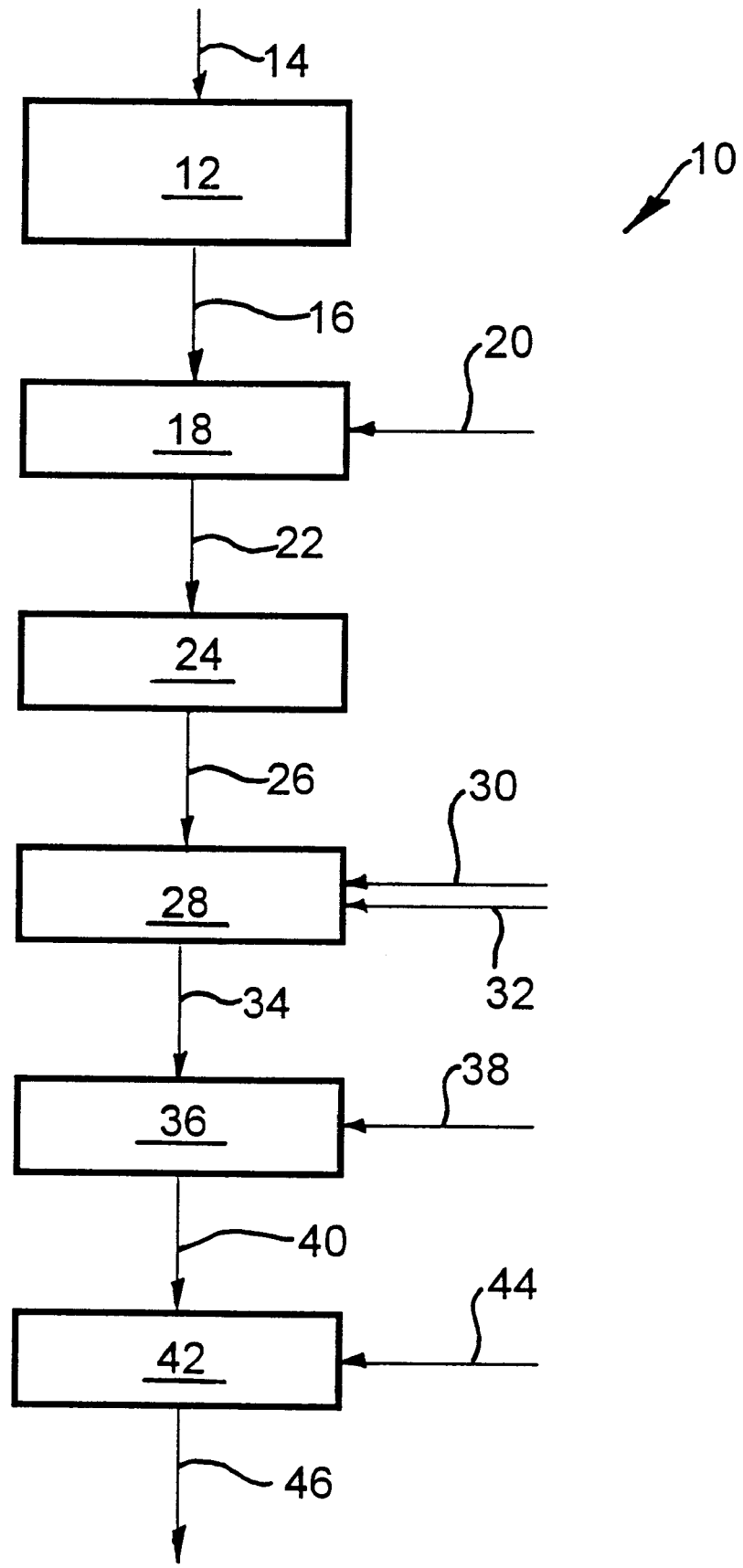

CATALYST SYSTEM SUITABLE FOR USE IN THE METATHESIS OF UNSATURATED HYDROCARBONS

CROSS-REFERENCE TO RELATED APPLICATIONS

This application is a divisional of U.S. application Ser. No. 08/708,173, filed Sep. 6, 1996, which claims priority from U.S. Provisional application Ser. No. 60/003,481, filed Sep. 8, 1995.

BACKGROUND OF THE INVENTION

According to a first aspect of the invention, there is provided a process for treating unsaturated hydrocarbons, which process comprises subjecting an unsaturated hydrocarbon component to metathesis in the presence of a catalyst system comprising silica, alumina and an alkyl tin compound, thereby to form one or more different hydrocarbons.

In principle, any unsaturated hydrocarbons can be treated in the process of the invention. However, the unsaturated hydrocarbon component may particularly comprise an internal olefin, such as 2-octene; an external olefin, such as 1-octene; or an unsaturated cyclic hydrocarbon, such as norbornene.

The metathesis reaction which takes place in the presence of the catalyst system involves breaking carbon-carbon double bonds and rearranging the resultant radicals to form the different or more desired hydrocarbons, which are usually also unsaturated. When an olefin hydrocarbon is used as feedstock, the following generalized metathesis reaction can take place:

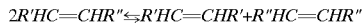

where R' and R" represent hydrocarbon radicals.

The more desired hydrocarbons which are formed are dependent primarily on the particular unsaturated hydrocarbon used as feedstock. Thus, if 1-octene is used as feedstock, the more desired hydrocarbons formed are primarily 7-tetradecene and ethene.

When an unsaturated cyclic hydrocarbon is used as feedstock, then the metathesis reaction usually involves ring opening polymerization.

The catalyst system may comprise a silica-alumina compound or substance as a first component, with the alkyl tin compound admixed therewith as a second component.

The first component thus comprises a silica-alumina compound or substance having the formula $SiO_2.Al_2O_3$. The proportion of $SiO_2$ to $Al_2O_3$ therein can vary, but it is believed that when the molar ratio of $SiO_2:Al_2O_3$ in the first component of the catalyst system is between 77:23 and 75:25, good results will be obtained, due to the strong acidic nature thereof.

The first component is preferably activated thermally before the second component is admixed therewith. This may be effected by treating the first component with oxygen at elevated temperature, eg at about 500° C., for a period of time, eg about 3 hours, and thereafter with nitrogen, also at elevated temperature, eg at about 500° C., for a period of time, eg about 2 hours.

To enhance the activity and/or the selectivity of the resultant catalyst system, the first component may, before the thermal activation thereof, be treated, eg impregnated, with phosphate ions and/or with cesium ions.

The admixing of the second component with the first component may be effected at room temperature.

The second component thus has the formula $SnR_4$, where R is an alkyl group. In particular, R may be methyl, ie Me.

The proportion of $SnMe_4$ to $SiO_2.Al_2O_3$ may be about $5.5 \times 10^{-5}$ mol $SnMe_4$/1g $SiO_2.Al_2O_3$ in the case where the first component is not pretreated with ions as hereinbefore described. When the first component contains 2% (mass basis) phosphate ($PO_4^{3-}$) ions, then the proportion of $SnMe_4$ to $SiO_2.Al_2O_3$ may be about $6.2 \times 10^{-5}$ mol $SnMe_4$/1g $SiO_2.Al_2O_3$.

The catalyst system preferably contains no transition metal, eg contains no tungsten, molybdenum or rhenium.

The metathesis may be effected at room temperature and at about atmospheric pressure.

According to a second aspect of the invention, there is provided a catalyst system suitable for use in the metathesis of unsaturated hydrocarbons, the catalyst system comprising silica, alumina and an alkyl tin compound in intimate contact with one another.

The catalyst system may thus be as hereinbefore described.

According to a third aspect of the invention, there is provided a method of making a catalyst system suitable for use in the metathesis of unsaturated hydrocarbons, the method comprising admixing a silica-alumina compound with an alkyl tin compound, to obtain a catalyst system comprising silica, alumina and an alkyl tin compound.

The method of making the catalyst system may thus be as hereinbefore described.

BRIEF DESCRIPTION OF THE DRAWING

The invention will now be described in more detail with reference to the accompanying simplified flow diagram of a process according to the invention for treating unsaturated hydrocarbons, and with reference to the non-limiting example.

In the drawing, reference numeral 10 generally indicates a process according to the invention for treating 1-octene.

DETAILED DESCRIPTION OF THE INVENTION

The process includes a silica-alumina ($SiO_2.Al_2O_3$) substance drying stage 12, with a silica-alumina substance flow line 14 leading into the stage 12. A flow line 16 leads from the stage 12 to a pretreatment stage 18, with an ammonium hypophosphate (($NH_4)_2HPO_4$) solution addition line 20 also leading into the stage 18. A flow line 22 leads from the stage 18 to a further drying stage 24.

A flow line 26 leads from the stage 24 to a thermal treatment stage 28, which can be in the form of a furnace or the like. An oxygen flow line 30 leads into the stage 28 as does a nitrogen flow line 32.

A flow line 34 leads from the stage 28 to a stage 36 with a alkyl tin compound addition line 38 leading into the stage 36.

A flow line 40 leads from the stage 36 to a metathesis reaction stage 42, with a 1-octene addition line 44 leading into the stage 42. A product withdrawal line 46 leads from the stage 42.

In use, a silica-alumina ($SiO_2.Al_2O_3$) is fed into the stage 12. It is dried in the stage 12, which may be in the form of an oven, at about 100° C. for about 1 hour. The dried silica-alumina then passes along the flow line 16 to the stage 18 where an aqueous solution of ($NH_4)_2HPO_4$, entering along the flow line 20, is mixed therewith. The moist product passes along the flow line 22 to the stage 24, which may also be in the form of an oven. It is dried in the stage 24 at about 100° C. for about 24 hours. The dried silica-alumina then passes along the flow line 26 to the stage 28 where it is activated. This is effected by first drying it under an oxygen atmosphere at a temperature of about 500° C., for about 3 hours, and thereafter under a nitrogen atmosphere, at the same temperature, for about 2 hours.

The activated silica-alumina product is then allowed to cool under nitrogen to room temperature, whereafter it passes along the flow line 34 to the stage 36 where a solution of SnMe$_4$ in chloro-benzene is added thereto. It is allowed to react with the SnMe$_4$ for about 5 minutes, whereafter the resultant catalyst passes along the flow line 40 to the metathesis reaction stage 42. 1-octene is added to the stage 42 along the flow line 44. The metathesis reaction is allowed to carry on for 5 up to 24 hours, whereafter the product is withdrawn along the flow line 46.

EXAMPLE

The process 10 was simulated on laboratory scale as follows: A silica-alumina mineral substance, containing SiO$_2$ and Al$_2$O$_3$ in a molar proportion of about 25–75, and being in the form of extrudates having an average diameter of about 1,0 mm–1,5 mm was dried at about 100° C. in an oven, for approximately 1 hour. An aqueous solution of 0,085 g (NH$_4$)$_2$HPO$_4$ in 4 ml water was added to 3 g of the dried silica-alumina, and the resultant mixture dried at 100° C. for 24 hours.

0,11 g of this dried sample was then placed in a glass test tube in a tubular furnace. It was heated at 500° C. under an oxygen atmosphere for 3 hours, and thereafter for a further 2 hours under a nitrogen atmosphere at the same temperature. The sample was transferred, under nitrogen, to a flask, and allowed to cool, while maintaining the nitrogen atmosphere, to room temperature. A solution comprising 6,2×10$^{-6}$ mol SnMe$_4$ in 1 cm$^3$ chloro-benzene was added to the cooled silica-alumina component, and allowed to react therewith for 5 minutes. Thereafter 2×10$^{-3}$ mol 1-octene was added thereto, and the mixture stirred for 24 hours at room temperature and at substantially atmospheric pressure. The liquid product was separated from the residual catalyst system, and GC analyzed. It was found to comprise, on a molar basis, 46,4% 1-octene, 1,2% tridecene and 23,3% tetradecene, with a 87% selectivity towards tetradecene. The balance was ethene.

The primary reaction was thus

$$2C_8H_{16} \rightarrow C_2H_4 + C_{14}H_{28}$$

It is believed that the catalyst system comprising silica-alumina and the methyl tin compound has advantages, in the metathesis of unsaturated hydrocarbons, over known transition metal systems in that it is less expensive and can be activated at a substantially lower temperature. It also has good activity and selectivity.

What is claimed is:

1. A catalyst system suitable for use in the metathesis of unsaturated hydrocarbons, the catalyst system comprising silica, alumina and an alkyl tin compound, with said catalyst system containing no transition metal and the molar rat of silica to alumina being at least 75:25.

2. A catalyst system according to claim 1, wherein said silica and alumina are present as a silica-alumina compound having the formula SiO$_2$.Al$_2$O$_3$, said alkyl tin compound having the formula SnR$_4$, where R is an alkyl group, and being admixed with said silica-alumina compound.

3. A catalyst system according to claim 2, wherein the molar ratio of silica to alumina in said silica-alumina compound is between 77:23 and 75:25.

4. A catalyst system according to claim 1, wherein, in said alkyl tin compound, R is methyl(Me), with the proportion of SnMe$_4$ to SiO$_2$.Al$_2$O$_3$ being about 5.5×10$^{-5}$ mol SnMe$_4$/g SiO$_2$.Al$_2$O$_3$.

5. A catalyst system according to claim 1, wherein said silica-alumina compound contains-phosphate ions and/or cesium ions impregnated therein.

6. A catalyst system according to claim 5, wherein, in said alkyl tin compound, R is methyl(Me), with said silica-alumina compound containing 2% by mass, based on the mass of the silica-alumina compound, phosphate (PO$_4^{3-}$) ions, and with the proportion of SnMe$_4$ to SiO$_2$.Al$_2$O$_3$ being about 6.2×10$^{-5}$ mol SnMe$_4$/g SiO$_2$.Al$_2$O$_3$.

7. A method of making a catalyst system suitable for use in the metathesis of unsaturated hydrocarbons, the method comprising admixing a silica-alumina compound with an alkyl tin compound to obtain a catalyst system comprising silica, alumina and an alkyl tin compound, with said catalyst system containing no transition metal and the molar ratio of silica to alumina being at least 75:25.

8. A method according to claim 7, wherein, in said catalyst system, said silica and alumina are present in said silica-alumina compound, said silica-alumina compound having the formula SiO$_2$.Al$_2$O$_3$, said alkyl tin compound having the formula SnR$_4$, where R is an alkyl group, and being admixed with the silica-alumina compound, and wherein the molar ratio of silica to alumina in said silica-alumina compound is between 77:23 and 75:25.

9. A process according to claim 8, wherein said silica-alumina compound is activated thermally before said alkyl tin compound is admixed therewith, by treating said silica-alumina compound with oxygen at an elevated temperature of about 500° C. For a period of time of about 3 hours, and thereafter treating it with nitrogen, also at an elevated temperature of about 500° C. For a period of time of about 2 hours.

10. A method according to claim 9, wherein said silica-alumina compound is, before the thermal activation thereof, impregnated with phosphate ions cesium ions or both, the admixing of said alkyl tin compound with said silica-alumina compound being effected at room temperature.

* * * * *